United States Patent [19]

Allard et al.

[11] 4,023,757
[45] May 17, 1977

[54] PATIENT CONTROLS HOLDER

[76] Inventors: Charles D. Allard, 6853 Payne Court, Pleasanton, Calif. 94566; Eugene R. Allard, 840 Delano Ave., San Lorenzo, Calif. 94580

[22] Filed: Mar. 5, 1976

[21] Appl. No.: 664,377

[52] U.S. Cl. .................................. 248/70; 248/160; 248/226.4; 248/311.3; 211/60 R

[51] Int. Cl.² ............................................ F16L 3/08

[58] Field of Search ............... 248/51, 52, 70, 160, 248/104, 274, 226 A, 311 A, 68 R, 74 A; 211/60 T, 60 R, 69, 95, 163, 70; 5/92; 312/209

[56] References Cited

UNITED STATES PATENTS

| 1,739,910 | 12/1929 | Livergood | 248/104 |
|---|---|---|---|
| 1,939,968 | 12/1933 | Frei | 248/160 |
| 2,696,963 | 12/1954 | Shepherd | 248/311 A |
| 2,935,286 | 5/1960 | Parsons | 248/311 A |
| 2,957,187 | 10/1960 | Raia | 248/311 A |
| 3,279,008 | 10/1966 | Wallach | 24/204 |
| 3,410,512 | 11/1968 | Delvecchio et al. | 248/104 |
| 3,460,789 | 8/1969 | McKirdy et al. | 248/311 A |
| 3,472,389 | 10/1969 | Lowe | 211/95 |
| 3,709,372 | 1/1973 | Alexander | 248/311 A |

Primary Examiner—Robert A. Hafer
Attorney, Agent, or Firm—James R. Cypher

[57] ABSTRACT

A holder for removable attachment to a hospital bed for releasably holding control devices operated by the patient consisting briefly of an elongated flexible and positionable member attachable at one end to the frame of the bed and having a head at the other end formed with slotted openings for receiving electrical and other types of cords or tubular hoses.

7 Claims, 7 Drawing Figures

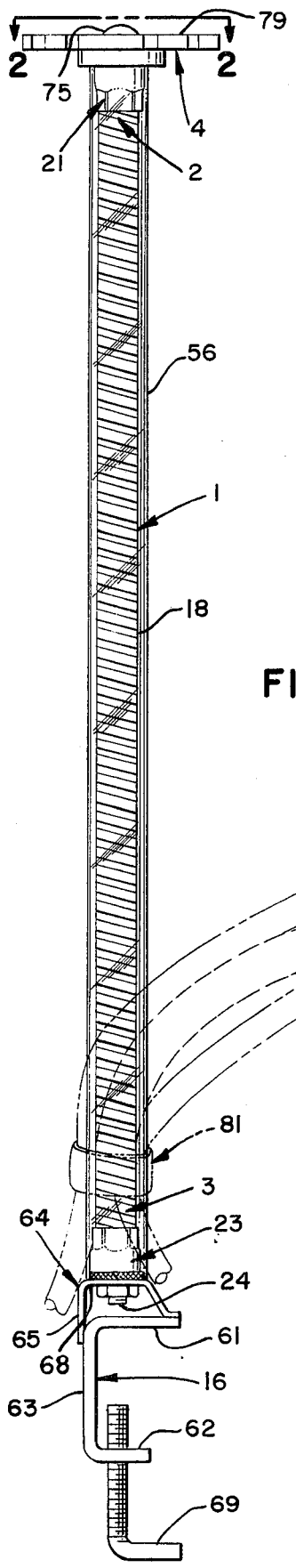
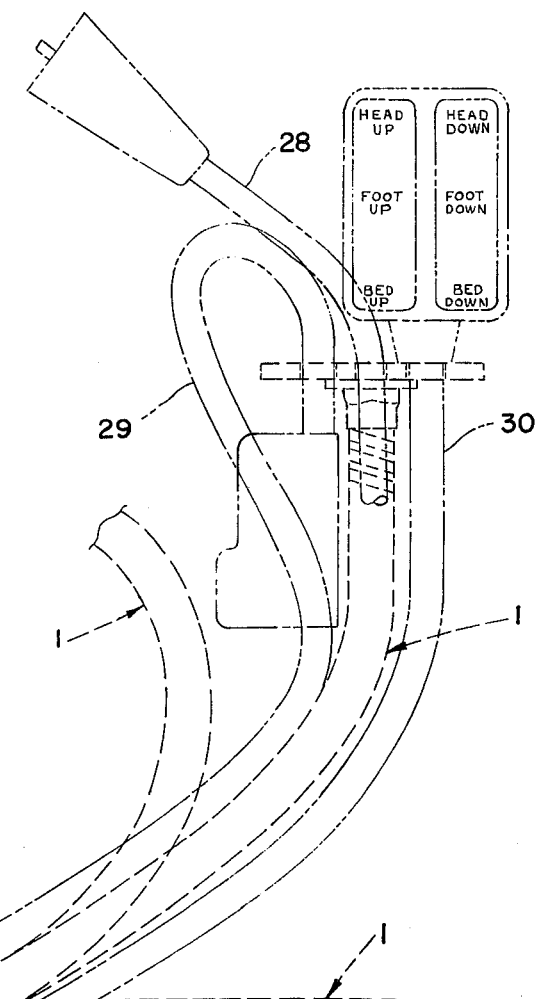
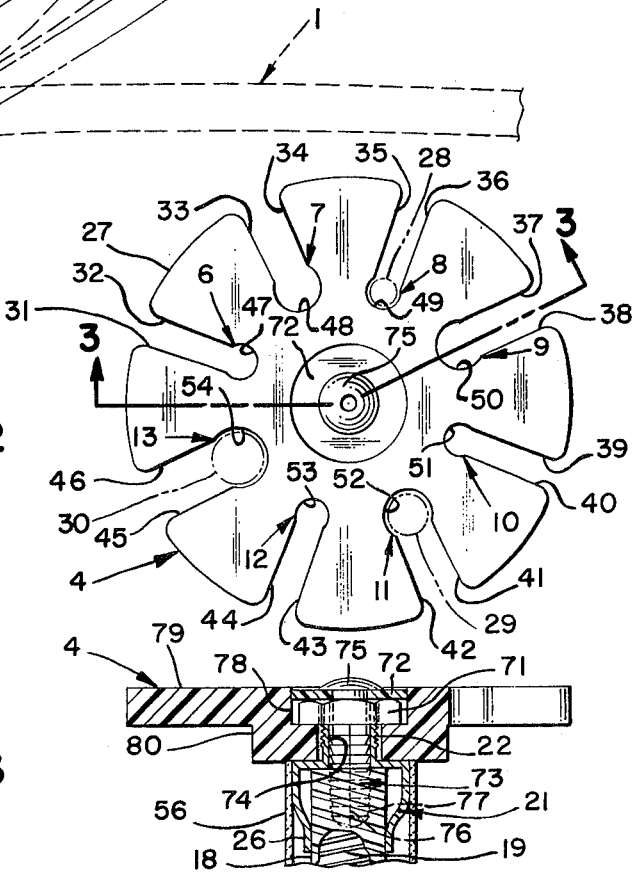
FIG. 1
FIG. 2
FIG. 3

PATIENT CONTROLS HOLDER

BACKGROUND OF THE INVENTION

Modern hospital beds may be raised and lowered by electrical motors. The push button control member may be placed into socket wells, located at the side and foot of the bed. Because it is difficult for patients to reach these controls, the controls are usually removed from the provided holders, and along with nurse call and television controls, are tied to bed side rails or clipped and pinned to bed sheets, to make them more accessible to the patient.

It is standard hospital procedure to keep bed side rails free from obstructions, so the patient can be attended to quickly in emergencies.

Controls that are tied to side rails often get caught and jammed between rail and bed frame causing severed cords and damaged controls.

Controls that are pinned and clipped to bed linens cause extensive damage to sheets, pillow cases, and controls. Such procedures can result in hindering the procedures necessary to reach the patient quickly, since the cords must be unclipped, unpinned or untied to get the controls out of the way and attend to the patient.

In recent years, more and more hospitals have installed television in the wards and rooms. In order to cause the least disturbance to other patients, the television control unit and the sound speaker are mounted in an expensive control unit connected to the television set by a long cord. This cord is also attached to the bed sheets by a metal or plastic clip or tied to the side railing. The TV control unit is fairly heavy and causes considerable damage to sheets. Further, senile patients often will roll over onto the metal or plastic clip or unit causing injury to themselves or damage to the unit if they urinate on it. Such control units cost between $60 and $80 and are difficult to repair and costly to replace.

In addition to the electrical cords above mentioned, it can be easily seen that in the future, as hospital labor costs escalate, it will be inevitable that more control units with their cords will become a part of the equipment which will be attached to the bed so that the patient can take care of himself to a greater extent.

In addition to electrical control unit cords, some hoses are occasionally taped to the bed or attached to the side rails such as oxygen tubes, IV tubing, and oxygen and other body function monitoring cords.

In short, the hospital bed has become a sophisticated apparatus with a myriad of cords and hoses, but hospital bed manufacturers have failed to provide a functional apparatus for holding these control units.

BRIEF SUMMARY OF THE INVENTION

The gist of the present invention is a holder which can conveniently hold all of the control units normally associated with the care of hospitalized bed ridden patients. The main feature of the holder is its ability to place the controls within easy reach of the patient yet be instantly moved out of the way in the event of an emergency without damage to the controls.

A further object is to provide a holder which holds a plurality of control units firmly and safely at all times even when the head of the bed is raised or lowered.

Another feature of the holder is the fact that its position can be easily and quickly adjusted by either the patient or the nurse simply by applying a slight pressure against the unit. No clamping, pinning twisting or levers are required.

An advantage of the present invention is the savings which result from the elimination of torn and worn bed sheets caused by metal clips and clamps of previous control holders.

Still another advantage is the better care that can be given to patients in an emergency since the control units can be instantly and safely removed from the patient so that the doctor or other persons can render emergency treatment.

A still further advantage is the elimination of damage to the patient controls caused by tying of controls to bed siderails, accidental dropping of controls and accidental liquid spillage on the controls.

A further advantage is the ability to quickly clamp the holder to either side of the bed without tools.

Still another advantage is the replacement of several clips and clamps for various control units by a single holder, thus eliminating the cost of ordering, stocking and repairing several different items.

Another feature of the present invention is the fact that it may be covered with a dielectric material thereby greatly reducing the probability of electrical shock.

A still further advantage is that by using the present holder, all of the patient controls can be taken off the bed and raised above it, thereby practically eliminating accidents caused by the patients rolling onto the controls.

BRIEF DESCRIPTION OF THE DRAWINGS

FIG. 1 is a side elevation view of the device of the present invention. To illustrate the usage of the device, the broken lines show the device positioned in three out of an infinite number of positions and with some illustrative control devices attached to the device.

FIG. 2 is a plan view of a portion of the device shown in FIG. 1 as taken along line 2—2. The broken lines indicate the relationship between the device and the cords of various control devices.

FIG. 3 is a cross section of a portion of the device taken along line 3—3 of FIG. 2.

DESCRIPTION OF THE PREFERRED EMBODIMENTS

Figure 4:
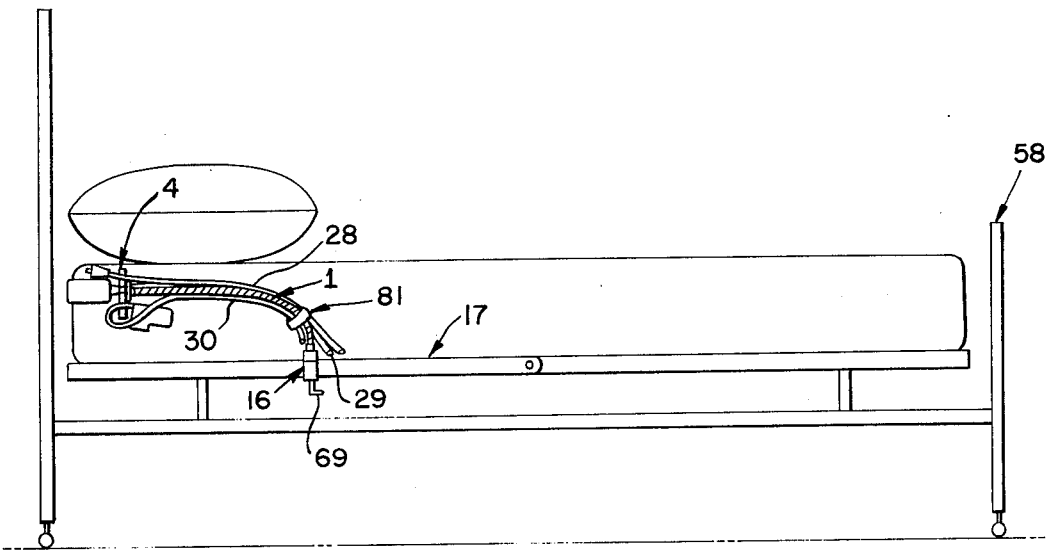
FIG. 4 is a side elevation view of the device mounted on a hospital bed. For illustrative purposes, several control devices are being held by the device in a position so that medical personnel may have unobstructed access to the patient.

The patient controls holder of the present invention consists briefly of an elongated flexible and positionable member 1 having a head end 2 and a foot end 3; a head member 4 connected to the head end of the elongated member and formed with electrical cord engaging holders 6, 7, 8, 9, 10, 11, 12, and 13; and means 16 connected to the foot end of the elongated member adapted for attachment to a structure 17.

We have found that the most suitable construction for the elongated member consists of a coiled metal sheath 18 surrounding a coil spring 19. The elongated member is commercially available from Eagle Manufacturing Company Of New York and is known as Ferry's Flexible Arm after the original inventor. The flexible arm is familiarly seen in the so called "goose neck" lamp. The elongated member can be bent in the shape of a compound curve and will stay in the position in which it is shaped. The internal coil spring prevents the member from kinking by being fashioned in too sharp a bend.

The elongated member is formed with a fitting 21 at the head end with male pipe threads 22 and a fitting 23 at the foot end with male pipe threads 24. The fitting is attached to the elongated member by a crimp fitting 26 or other suitable fastening.

The head member as stated above is formed with a plurality of holders which preferably are slots opening to the outside edge 27 of the head for holding electrical cords as for example, cords 28, 29 and 30. Preferably the slots are formed along radians in a disc-like member. The slots consist of parallel sides 31, 32, 33, 34, 35, 36, 37, 38, 39, 40, 41, 42, 43, 44, 45, and 46 and terminate at their inner ends in generally circular shaped openings 47, 48, 49, 50, 51, 52, 53, and 54 having a size slightly greater in diameter than the width of the slots. All the slots have a width 1/32 inch less than the circular opening so that the electrical cords or other tubes will not slip out of the circular openings. The circular openings may be sized to accommodate the particular cords and tubes commonly used. Some representative sizes for the round openings are as follows: Opening 47—7/32 inch, opening 48—19/64 inch, opening 49—7/32 inch, opening 50—19/64 inch, opening 51—7/32 inch, opening 52—19/64 inch, opening 53—7/32 inch, and opening 54—13/32 inch. All edges of the slots are, of course, beveled and smoothed to prevent damage to the cords or tubes. Dimensions of the head will vary but we have found that a disc of about 3 inches with a thickness of about ¼ inch is most satisfactory. The head member may be made of various materials. Preferably the head member is made from a di-electric material to prevent shock should the cord be accidentally severed or the insulation on the cord become worn. A suitable material is an ABS Plastic "cycolac" which has rubber in it, is resilient and is manufactured by the Borg-Warner Company.

In order to further prevent injury from electrical shock, the elongated member is sheathed in a plastic sheath 56.

The means connected to the foot of the elongated member is preferably a clamp for engaging an angular frame member 17 of a hospital bed 58. The clamp is specially constructed so that it can be fitted to either side of the bed and will fit most every size and style of hospital bed. Basically, the clamp consists of a C-shaped member having an upper leg 61 and a lower leg 62, joined by a section 63. A "hat" member 64 is attached to the C-shaped member as by welding and consists of a leg 65 attached to leg 61 and a leg 66 formed at an angle so that it will contact the mattress at an angle rather than abruptly to prevent damage to the mattress 67. A section 68 joins the two legs and is formed with an opening for receiving the threaded end 24 of fitting 23. Leg 62 is formed with a threaded opening for receiving threaded crank 69.

The head member 4 is attached to the elongated flexible member by threaded nut 71 on male threads 22. To prevent electrical shock, it is preferable to cover nut 71, if it is metal, with dielectric washer 72. The washer may be secured by inserting plastic fastener 73 into opening 74 in fitting 21. Fastener 73 has an enlarged head 75 and a split shank 76 formed with "arrow-head" serrations 77 to prevent accidental withdrawal.

The head member may be formed with a countersunk opening 78 so that the nut 71 and washer 72 will not protrude above the top face 79 of the head member. To insure a lightweight member, the lower portion 80 of the head member may be diminished in diameter as shown in the drawings.

Figure 5:
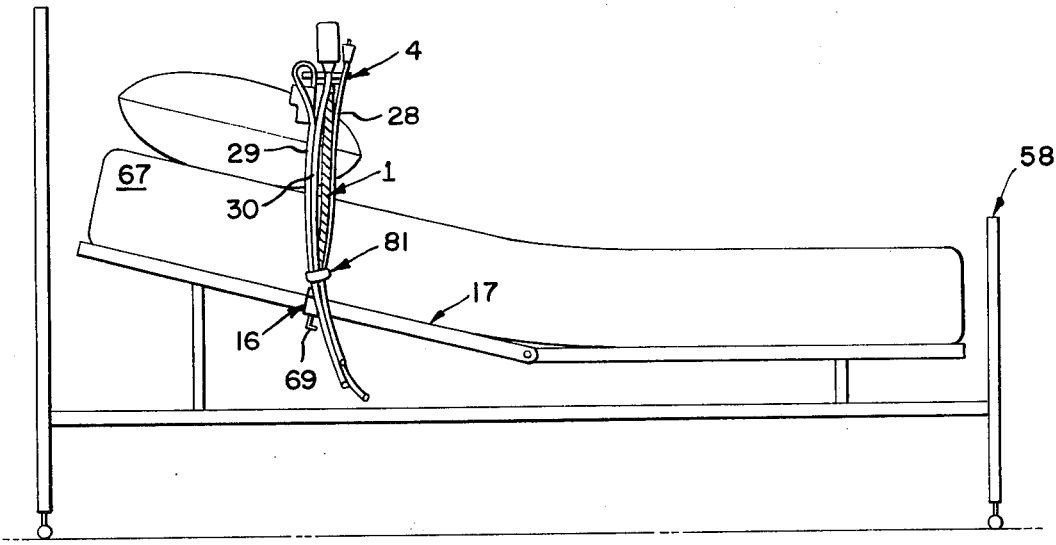
FIG. 5 is a side elevation view of the device similar to FIG. 4 but with part of the bed in the raised position and the device positioned for access by the patient.
Figure 6:
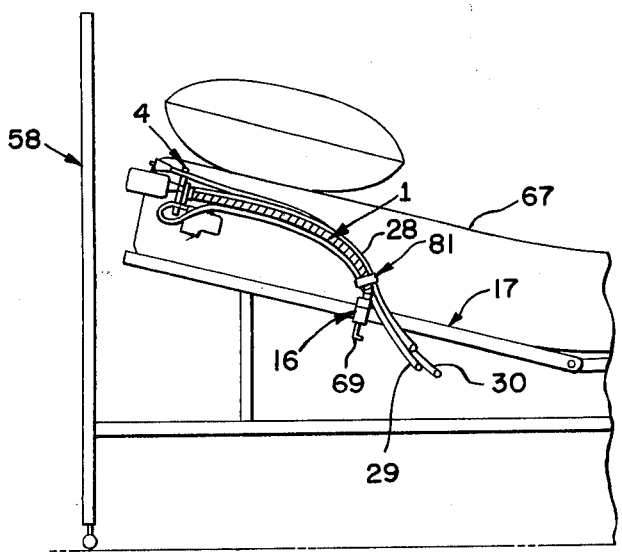
FIG. 6 is a side elevation view of the device with the bed in the partially raised position and the device in the folded position for access by medical personnel to the patient.
Figure 7:
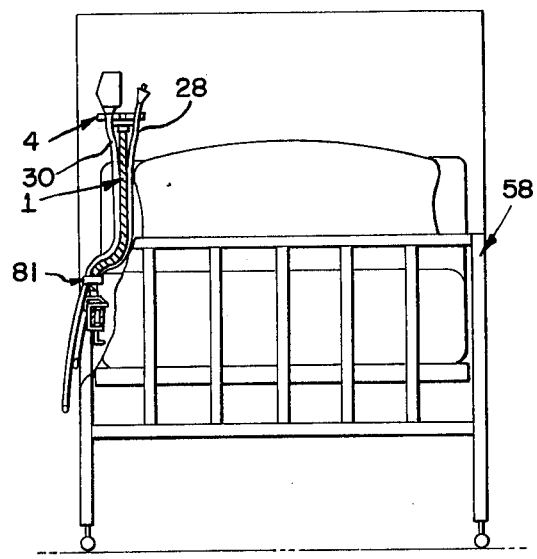
FIG. 7 is an end view of the device mounted on a bed with the bed in the horizontal position and the device positioned for easy access by the patient.

The operation of the device is shown in FIGS. 1, 4, 5, 6, and 7. The device is first connected to either side of a bed such as the frame angle 17. The device is then positioned in an upright manner to receive the cords of the control devices such as the call button, the bed raising mechanism, the TV control mechanism or other control devices. Next the elongated member is placed in the desired position, either out of the way, as shown in FIGS. 4 and 6 or in a position so as to make the control devices accessible to the patient as shown in FIGS. 5 and 7.

In order that the cords will follow the contour of the elongated member, a clasp means such as a strap 81 with a fastening means such as a snap or "Velcro" may be attached to the elongated member. The strap can be wrapped around all of the electrical cords as shown in FIGS. 1, 4, 5, 6 and 7.

As previously described, the elongated member will take an infinite variety of positions and will stay in the position selected.

We claim:

1. A holder device for holding control members having electrical cords of differing diameters to hospital beds, furniture, or shelving comprising:
   a. an elongated flexible and positionable member having a head end and a front end;
   b. a head member formed from a di-electric material connected to the head end of said elongated member formed with a plurality of slots of differing selected widths adapted for holding a plurality of said electrical cords of selected differing diameters;
   c. said slots are defined by parallel side walls extending from the outer perimeter of said head to a generally circular opening positioned inwardly from said perimeter head;
   d. the distances between each of said parallel side walls is selected to forcibly accept an electrical cord of standard diameter and to reject all cords not of said selected standard diameter;
   e. said generally circular openings are dimensioned to frictionally hold said electrical cords of different standard sizes in a frictional grip to prevent slippage therethrough after positioning and have diameters slightly greater than the widths of said slots with which they connect; and
   f. connection means connected to the foot end of said elongated member adapted for attachment to said hospital beds, furniture or shelving.

2. A holder as described in claim 1 comprising:
   a. said elongated member consists of a coiled metal sheath surrounding a coil spring.

3. A holder as described in claim 2 comprising:
a. a plastic sheath member enclosing said metal elongated member.

4. A holder as described in claim 1 comprising:
a. clasp means having a first open position slidably attached to said elongated member and a second closed position for clasping said cords in close relation to said elongated member at a selected point along said elongated member.

5. A holder as described in claim 4 comprising:
a. said clasp means consists of a length of Velcro material.

6. A holder as described in claim 4 comprising:
a. said head member is rotatably mounted on said elongated member; and
b. said clasp means is selected to clamp said cords to said elongated member with sufficient force to prevent rotation of said head with respect to said elongated member.

7. A holder as described in claim 1 comprising:
a. said connection means connected to said foot end of said elongated member forms a clamp which includes a channel member formed with a threaded opening in one side and a threaded hand engageable tightening member for threadable receipt therein; and
b. a hat-shaped member attached to said channel member side opposite said threaded opening and having an opening therethrough for receiving the foot end of said elongated member; and
c. said hat shaped member is formed with an angled side member for abuttment against a bed mattress.

* * * * *